(12) United States Patent
Keil

(10) Patent No.: US 10,779,759 B2
(45) Date of Patent: Sep. 22, 2020

(54) LANCING AID HAVING AUTOMATIC TRIGGERING

(71) Applicant: ROCHE DIABETES CARE, INC., Indianapolis, IN (US)

(72) Inventor: Michael Keil, Limburgerhof (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 758 days.

(21) Appl. No.: 13/663,729

(22) Filed: Oct. 30, 2012

(65) Prior Publication Data
US 2013/0085517 A1 Apr. 4, 2013

(30) Foreign Application Priority Data
Apr. 30, 2010 (EP) .................................. 10004578

(51) Int. Cl.
*A61B 5/151* (2006.01)
*A61B 5/15* (2006.01)

(52) U.S. Cl.
CPC .... *A61B 5/15163* (2013.01); *A61B 5/150022* (2013.01); *A61B 5/15111* (2013.01); *A61B 5/15117* (2013.01); *A61B 5/15128* (2013.01); *A61B 5/15146* (2013.01); *A61B 5/150412* (2013.01); *A61B 5/150519* (2013.01)

(58) Field of Classification Search
CPC .............. A61B 5/1411; A61B 5/15107; A61B 5/15109; A61B 5/15111; A61B 5/15113; A61B 5/15117; A61B 5/15146; A61B 5/15186; A61B 5/150022; A61B 5/150572
See application file for complete search history.

(56) References Cited

U.S. PATENT DOCUMENTS

| | | | |
|---|---|---|---|
| 4,661,546 A * | 4/1987 | Abu-Isa ................. | C08K 5/526 524/153 |
| 5,318,584 A * | 6/1994 | Lange et al. .................. | 606/182 |
| 6,540,762 B1 * | 4/2003 | Bertling ............... | A61B 5/1411 606/182 |
| 6,986,777 B2 | 1/2006 | Kim | |
| 7,273,484 B2 * | 9/2007 | Thoes ................ | A61B 5/15186 600/573 |
| 2002/0169470 A1 | 11/2002 | Kuhr et al. | |
| 2003/0050656 A1 | 3/2003 | Schraga | |
| 2003/0199892 A1 | 10/2003 | Kim | |
| 2004/0092996 A1 * | 5/2004 | List ...................... | A61B 5/1411 606/181 |

(Continued)

FOREIGN PATENT DOCUMENTS

| | | |
|---|---|---|
| EP | 0565970 A1 | 10/1993 |
| EP | 0668049 A1 | 8/1995 |

(Continued)

*Primary Examiner* — Wade Miles
*Assistant Examiner* — Kankindi Rwego
(74) *Attorney, Agent, or Firm* — Maschoff Brennan

(57) ABSTRACT

The present application concerns a system for the withdrawal of body fluids comprising a coupled tensioning and triggering mechanism, wherein the triggering mechanism is mechanically coupled to the tensioning mechanism in such a manner that the puncturing process is automatically triggered by successive continuation of the tensioning movement when the tensioning mechanism is actuated and wherein the lancing process triggered in this manner is carried out by a lancet.

13 Claims, 12 Drawing Sheets

(56) References Cited

U.S. PATENT DOCUMENTS

| | | |
|---|---|---|
| 2005/0090850 A1 | 4/2005 | Thoes et al. |
| 2005/0222599 A1 | 10/2005 | Czernecki et al. |
| 2006/0020189 A1* | 1/2006 | Brister ............... A61B 5/0002 600/345 |
| 2006/0293611 A1 | 12/2006 | Calasso et al. |
| 2007/0173741 A1* | 7/2007 | Deshmukh ........... A61B 5/1411 600/583 |
| 2008/0077168 A1* | 3/2008 | Nicholls ............ A61B 5/15142 606/182 |
| 2008/0195132 A1 | 8/2008 | Schraga |
| 2012/0022566 A1 | 1/2012 | Wilkinson |

FOREIGN PATENT DOCUMENTS

| | | |
|---|---|---|
| EP | 1034740 A1 | 9/2000 |
| EP | 1263320 B1 | 12/2002 |
| EP | 1384438 A1 | 1/2004 |
| EP | 1504718 A2 | 2/2005 |
| EP | 2033577 A1 | 3/2009 |
| WO | 0205872 A2 | 1/2002 |
| WO | 0236010 A1 | 5/2002 |
| WO | 2002036010 A1 | 5/2002 |
| WO | 03073936 A2 | 9/2003 |
| WO | 2008145625 A2 | 12/2008 |

* cited by examiner

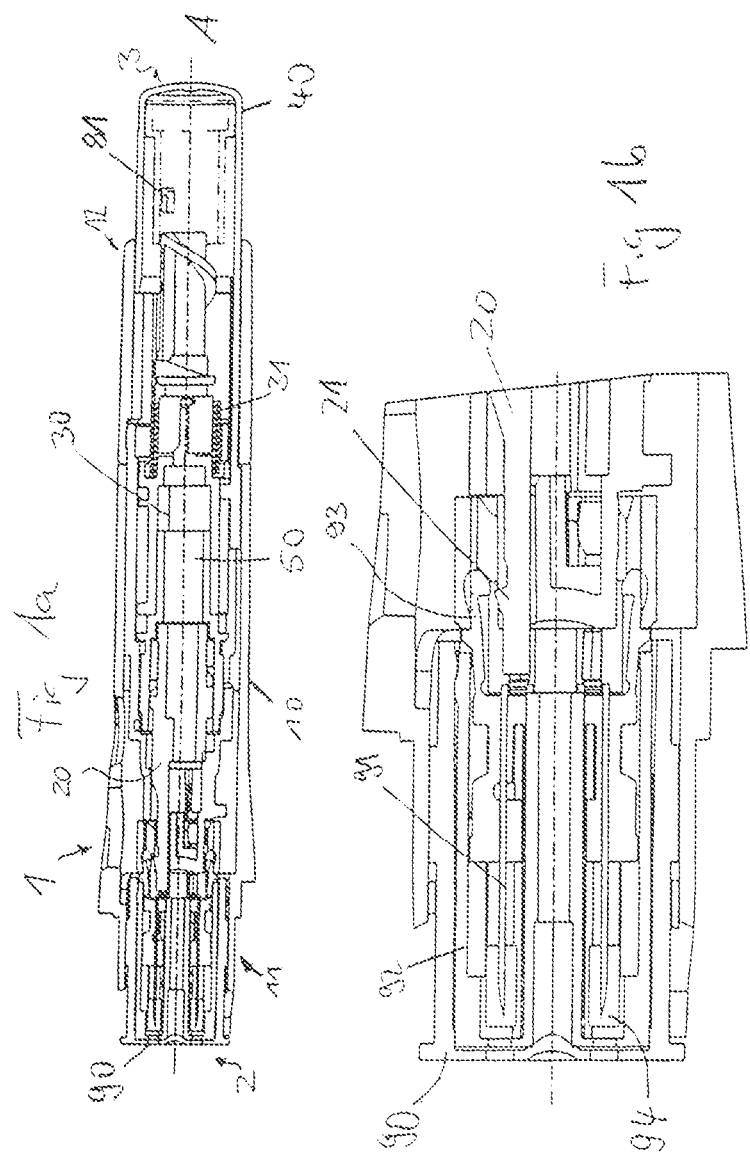

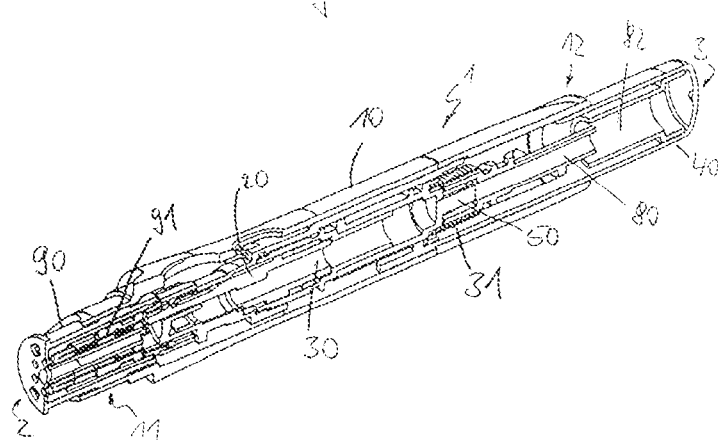

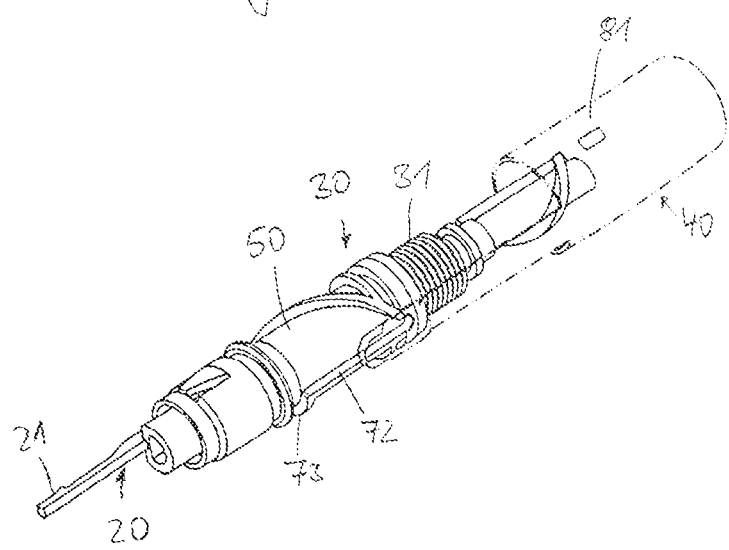

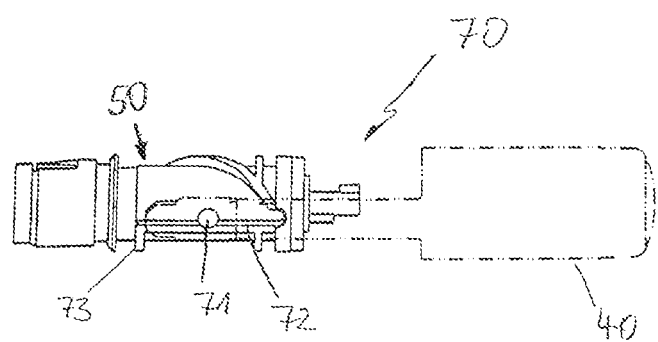

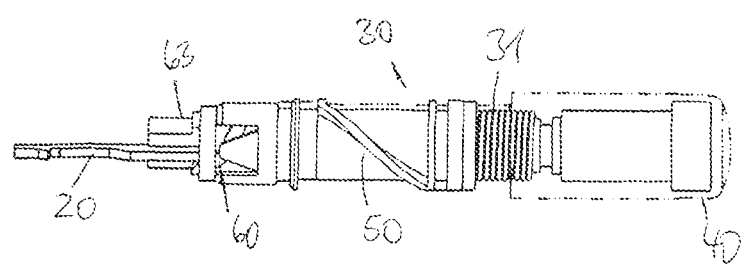

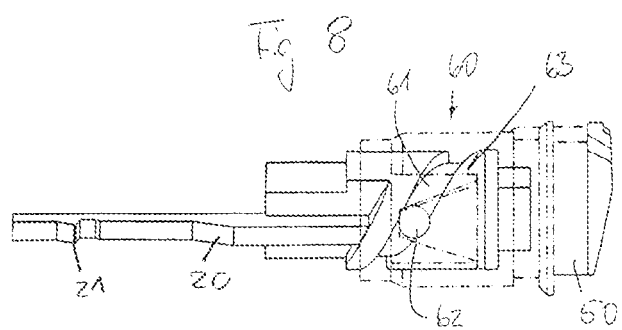

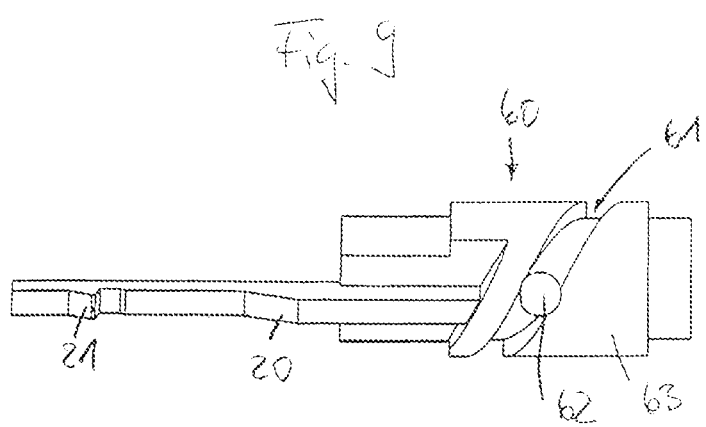

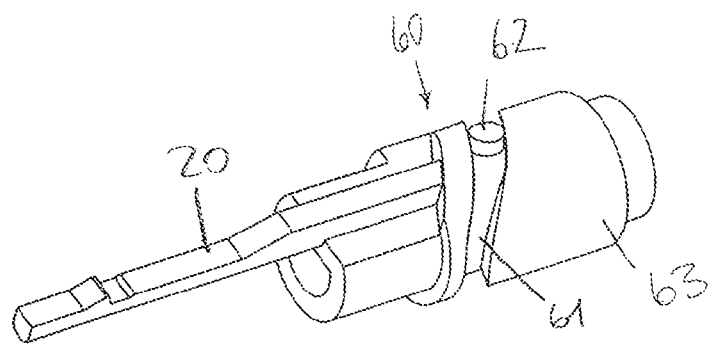

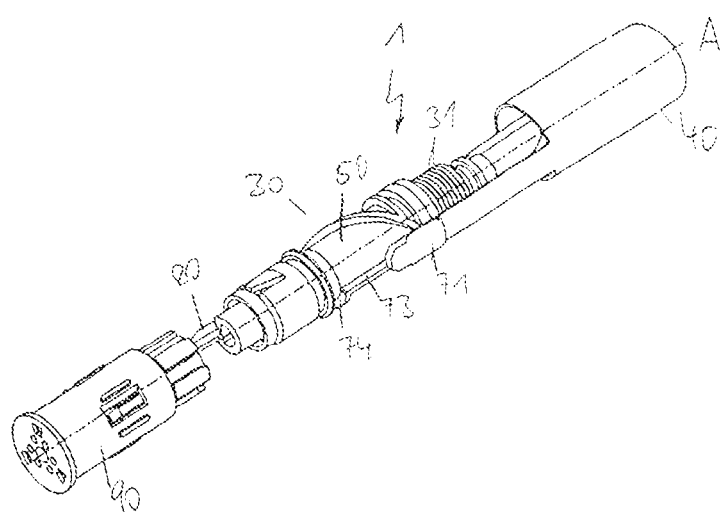

LANCING AID HAVING AUTOMATIC TRIGGERING

CROSS REFERENCE TO RELATED APPLICATIONS

The present U.S. utility patent application is related to and claims the priority benefit to patent cooperation treaty patent application serial no. PCT/EP2011/002083, filed Apr. 26, 2011, which claims priority to European Patent Application Serial No. 10004578.0, filed Apr. 30, 2010, the contents of which are hereby incorporated by reference in their entirety into this disclosure.

BACKGROUND

In the analysis and examination of various diseases, it is often necessary to examine body fluids and in particular human blood with regard to an analyte contained therein. In many cases it is sufficient for this purpose to remove a small amount of the desired body fluid from the body, such as a drop of blood, by generating a small puncture wound. A particularly important case of this kind is diabetes in which blood has to be examined for its glucose content at regular intervals. Further examinations of blood can for example be carried out with regard to the coagulation parameters, triglycerides, HbA1c or lactate. In order to generate the required puncture wounds, blood lancet devices are commonly used which consist of a lancing device and replaceable lancets that have been adapted thereto. In the housing of the lancing device there is a lancet holder in which one lancet can be used in each case in a replaceable manner. During the puncturing operation the lancet holder is moved rapidly in a puncturing direction by a lancet drive that is also integrated in the lancing device until the lancet tip emerges from an exit opening provided at the front end of the lancing device and generates a small puncture wound in the part of the body that is pressed against the front end. Afterwards the lancet holder together with the lancets is moved back against the lancing direction.

In addition to the use of blood lancet devices by medical staff, lancing aids are in addition also used by laymen in the so-called home-monitoring field. This applies especially to therapeutic monitoring by diabetics. Thus, in the treatment of diabetics it was found that serious damage associated with diabetes such as for example going blind can be significantly reduced if the glucose concentration in the blood of the diabetic is determined frequently up to five times daily and the insulin injection can be exactly adjusted on the basis of these measurements. In order to undertake such frequent measurements, lancing aids are used within the framework of home-monitoring so that the diabetic can carry out a blood analysis himself. The resulting requirements for a blood lancet device are also a simple handling when inserting new lancets and safe discarding of already used lancets in addition to a simple handling when triggering the puncturing operation and a low-pain puncture. A replacement of lancets should, on the one hand be as simple as possible but, on the other hand, ensure a maximum of safety against unintentional injury of the user or third persons. Although in the home-monitoring field it is conceivable that a lancet, once inserted, is used several times for lancing by the same user, even in this case an accidental re-use of an ejected lancet should be prevented once the user has decided to discard the lancet. Furthermore, other persons in particular should be reliably protected from the discarded lancets for example during waste disposal.

SUMMARY

In an exemplary embodiment of the present disclosure and a system for withdrawing body fluids is provided. The system including a withdrawal device and at least one lancet having a lancet body, a lancet tip, and a sterile protection which ensures the sterility of the unused lancets prior use in a punture, the sterile protection consisting of an elastomeric material which during the puncture is pierced or stripped of by the lancet tip. The system further including a housing with an exit opening for the lancet tip, the housing at least partially enclosing the withdrawal device. Additionally, the system includes a lancet holder which can be moved in the housing along a predetermined puncture path to replaceably hold the at least one lancet, a magazine containing the at least one lancet, wherein the at least one lancet can be successively coupled to the lancet holder, the magazine removably coupled to the housing. Moreover, the system further comprises a lancet drive, a lancet guide, and a combined tensioning and triggering device. The lancet drive having an elastic drive element which can be converted by tensioning from an untensioned into a tensioned state and by means of which after the triggering, the relaxing movement of the tensioned elastic drive element is converted into a lancing movement in the course of which the lancet held by the lancet holder is moved in a puncturing direction along the predetermined puncture path until the lancet tip emerges at least partially from the exit opening and by means of which the lancet holder is returned by the lancet drive into a position in which the tip of the lancet is located in the housing. The lancet guide structured to guide the lancet holder on the predetermined puncture path after the lancing movement is triggered. The combined tensioning and triggering device having an actuating element and a locking device, the actuating element having an initial state and an actuated state and being accessible from the outside of the housing, the locking device being mechanically coupled to the actuating element and the lancet drive in such a manner that the lancet drive is firstly tensioned and then released when the actuating element is moved along the actuation path where the release of the lancet drive is enabled when a certain point along the actuation path is reached, wherein the housing at least partially encloses the combined tensioning and triggering device.

In at least one exemplary embodiment of the present disclosure, the locking device is designed as a track control which comprises a control track part and a control cam as members wherein the control cam makes a relative movement with respect to the control track part during at least a part of the movement of the actuating element along the actuation path, in which it travels along at least part of the control track part of the track control.

In at least one exemplary embodiment of the present disclosure, the lancet drive has a rotary/sliding transmission comprising a rotatable drive rotor by means of which a turning moment introduced on the input-side of the rotary/sliding transmission is converted into a longitudinal displacement in the direction of a predetermined puncture path, wherein the drive rotor is coupled to the elastic drive element and longitudinal displacement of the rotary/sliding transmission on the output side is transferred onto the lancet holder.

In at least one exemplary embodiment of the present disclosure, the control track part of the track control is mounted at least partially on the drive rotor. Further, the control track part may comprise a first and a second section, wherein the first section of the control track part runs essentially parallel to the axis of rotation of the rotary sliding transmission and wherein the second section of the control track part runs essentially perpendicular to the axis of rotation of the rotary/sliding transmission.

In at least one exemplary embodiment of the present disclosure, the elastic drive element of the lancet drive is converted by continuous unidirectional displacement of the actuating element firstly from an untensioned into a tensioned state and is subsequently triggered.

In at least one exemplary embodiment of the present disclosure, the actuating element is an operating button protruding out of the rear end of the housing facing away from the exit opening for the lancet tip.

In at least one exemplary embodiment of the present disclosure, the rotary/sliding transmission has a cam control comprising a recess forming a guide curve that can be rotated together with the drive rotor into which a matching guide pin engages where at least a part of the puncturing and return movement is determined by a relative movement between the guide pin and the recess which the guide pin makes when it travels through the guide curve formed by the recess.

In at least one exemplary embodiment of the present disclosure, the input-side of the rotary/sliding transmission is formed by a helix provided on the rotatable transmission member and by a tensioning cam connected to the actuating element that can move along the actuation path and can slide on a slide surface of the helix by means of a contact surface.

In at least one exemplary embodiment of the present disclosure, the magazine contains a at least one lancet adapted to the withdrawal device, the plurality of lancets comprising a lancet body and a lancet tip and can be successively coupled to the lancet holder. The at least one lancet may each be furnished with a sterile protection which ensures the sterility of as yet unused lancets until the puncture. Further, the magazine may comprises at least part of the lancet guide.

In at least one exemplary embodiment of the present disclosure, the lancet is mechanically coupled to the lancet drive during the entire puncture process.

In at least one exemplary embodiment of the present disclosure, the system further comprises an indicating element for indicating the imminent triggering of the puncture movement. Additionally, the indicating element for indicating the imminent triggering of the puncture movement may be part of the actuating element.

BRIEF DESCRIPTION OF THE DRAWINGS

The features and advantages of the present disclosure, and the manner of attaining them, will be more apparent and better understood by reference to the following descriptions taken in conjunction with the accompanying figures, wherein:

FIG. 1a shows a cross-section of an embodiment of a system according to the present disclosure with a lancet magazine placed on it;

FIG. 1b shows a cross-sectional enlargement of the lancet magazine of the cross-section from FIG. 1a;

FIG. 2 shows a perspective view of a cross-section of the system from FIG. 1a;

FIG. 3 shows a perspective view of a withdrawal device of a system without a housing, according to at least one embodiment of the present disclosure;

FIG. 3a shows a separate view of the locking device, according to at least one embodiment of the present disclosure;

FIG. 7 shows a side-view of the rear side of the withdrawal device shown in FIG. 6;

FIG. 8 shows a detailed view of the transmission member on the output side with a lancet holder of the withdrawal device shown in FIGS. 3 to 7;

FIG. 9 shows a simplified diagram of the detailed view of the transmission member on the output side with the lancet holder of the withdrawal device shown in FIGS. 3 to 7 without a drive rotor;

FIG. 10 shows a perspective view of the lancet holder shown in FIGS. 8 and 9; and FIG. 11 shows a perspective view of the withdrawal device shown in FIG. 1a with a lancet magazine in place but without a housing.

DETAILED DESCRIPTION

Figure 4:
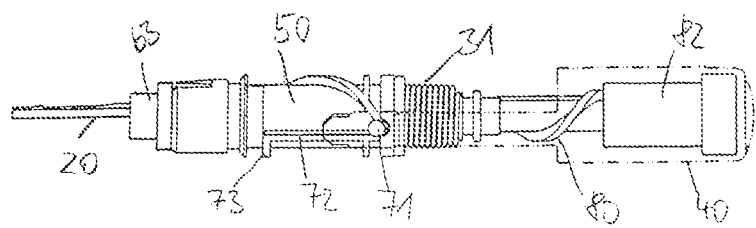
FIG. 4 shows a side-view of the withdrawal system from FIG. 3 before shifting the actuating element i.e. in the initial state.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In at least one embodiment of a device of the present disclosure, the exemplary comprises a coupled tensioning and trigger mechanism, wherein the trigger mechanism is mechanically coupled to the tensioning mechanism in such a manner that upon actuation of the tensioning mechanism the puncturing operation is automatically triggered by steady continuation of the tensioning movement, and wherein the puncturing operation triggered in this manner is executed by a lancet. The device in various embodiments may be referred to herein as a "lancing aid" and for withdrawing body fluids for diagnostic purposes.

According to at least one embodiment of the present disclosure, the exemplary embodiment is a lancing aid which can be operated
  with a minimal expenditure of force,
  in a manner that is as simple and intuitive as possible and
    in particular with the lowest possible number of operating steps,
  while generating the lowest possible puncture pain,
and which is characterized by good handling, in particular by particularly small outer dimensions as well as by the lowest possible number of additional components and by a resulting economical production. Moreover, an exemplary embodiment contributes towards reducing the inhibition threshold of a user with regard to generating a puncture wound.

Further, according to at least one embodiment of the present disclosure, a exemplary system comprises:
  a withdrawal device and at least one lancet adapted to the withdrawal device which has a lancet body and a lancet tip,
  a housing with an exit opening for the lancet tip, a lancet holder which can be moved in the housing along a predetermined puncture path to replaceably hold the lancet, a lancet guide for guiding the lancet holder on the predetermined puncture path after triggering the lancing movement, a lancet drive with an elastic drive element which can be converted by tensioning from an untensioned into a tensioned state and by means of which after the triggering, the relaxing movement of the tensioned elastic drive element is converted into a lancing movement in the course of which the lancet held by the lancet holder is moved in the puncturing direction along the predetermined puncture path until the lancet tip emerges at least partially from the exit opening and by means of which the lancet holder is returned into a position in which the tip of the lancet is located in the housing, and a combined tensioning and triggering device having an actuating element that is accessible from the outside of the housing which has an initial state and an actuated state where the combined tensioning and triggering device has a locking device which is mechanically coupled to the actuating element and the lancet drive in such a manner that the lancet drive is firstly tensioned and then released when the actuating element is shifted along the actuation path where the release of the lancet drive is enabled when a certain point along the actuation path is reached.

The system according to the present disclosure may be used in at least one embodiment for withdrawing body fluids, such as for example blood or interstitial fluid. Further, this may be conducted for diagnostic purposes. Since usually only very small amounts of body fluid, such as blood, to be examined are required for diagnostic purposes, the system according to the present disclosure serves to withdraw small amounts of the respective body fluid where the amount to be withdrawn may be in an amount of about 0.5 to about 5 µl, or in an amount from about 1 to about 3 µl.

In order to withdraw the small amounts of the selected body fluid an incision is made in a previously chosen skin region, for example a finger tip or earlobe, using an embodiment of the system according to the present disclosure. The desired incision is usually made by inserting an embodiment of the lancet that is part of the system, according to the present disclosure, as rapidly and quickly as possible into the selected skin region. As a result the desired small amount of the respective body fluid can emerge from the selected skin region.

At least one embodiment of the system of the present disclosure may be a re-usable system for withdrawing body fluids and blood (i.e. a system that is not designed for single use). Consequently, the system according to at least one embodiment of the present disclosure and more precisely the withdrawal device that is part of the system, can be used once or several times consecutively after replacing the lancet used in each case by an unused lancet.

In at least one embodiment of the system of the present disclosure, the system comprises a withdrawal device and at least one lancet adapted to the withdrawal device, which has a lancet body and a lancet tip. As already explained above, embodiments of the withdrawal device may be suitable for single use as well as for multiple use. Within the scope an exemplary embodiment, the system can be used several times optionally with repeated use of an already used lancet or after replacing an already used lancet by an as yet unused lancet. In such a case, a used lancet is understood as one with which one or more punctures have already been carried out.

Exemplary embodiments of the lancets according to the present disclosure, have a lancet tip and a lancet body which can have a one-piece as well as a multiple-piece design. In the case of a multiple-piece design, the lancet body and lancet tip can be made from the same material or from different materials. Metals such as for example stainless steel or special spring steel are suitable materials for the lancet tip. In at least one embodiment, an exemplary lancet may comprise a lancet tip made from stainless steel and are joined to a lancet body that is made from a suitable plastic, such as acrylonitrile butadiene styrene.

In addition, the lancets that are to be used within the scope of the system according to the present disclosure may have a protecting body which surrounds the lancet in such a manner that it is able to prevent contamination of the lancet tip with contaminants or germs and ensure the sterility of an as yet unused lancet. Such protecting bodies that are also referred to as a sterile protection are known to a person skilled in the art and are described for example in EP 1 263 320 A1. The exemplary sterile protection may be made from a suitable plastic and can be removed from the lancet tip either before using the lancet or also during use, i.e. during the puncture.

An exemplary system according to the present disclosure, and more specifically the withdrawal device that is part of the exemplary system, has a housing with an exit opening for the lancet tip. This housing may have an elongate shape that can has a main axis (A). The exit opening for the lancet tip is located at one end of the elongate housing. This end is referred to within the scope of the present disclosure as the proximal end.

The system according to the present disclosure may additionally includes a lancet holder to replaceably hold the lancet which can be moved in the housing along a predetermined, and potentially straight puncture path. This predetermined puncture path may in at least one embodiment be aligned parallel to the direction of the main axis (A) of the housing. The lancet holder provided according to the present disclosure is used to receive the lancet and may be designed such that it holds the lancet during the movement along the puncture path to make the aforementioned skin incision i.e. is in a permanent but detachable mechanical coupling with the lancet. Thus, the term "replaceably hold" is to be understood within the scope of the present disclosure to mean that the lancet holder is connected to the lancet at least during the puncturing operation in such a manner that the mechanical coupling between the lancet and the lancet body and lancet holder can be maintained continuously and can be released or maintained after completion of the puncturing operation. In this manner it is possible to either re-use or remove a lancet after a puncturing operation has been carried out and replace it by another lancet, which may be previously unused.

The mechanical coupling between the lancet and lancet holder can for example be achieved by means of a press fit or by clamping or locking A suitable lancet holder within the scope of the system according to the present disclosure is for example described in EP 0 565 970 A1. Accordingly, the lancet body can for example be surrounded by the lancet holder in a form-fitting manner. A form-fitting coupling between the lancet body and lancet holder is also possible when the lancet holder is designed as a push rod which has a holding device which makes a releasable form-fitting coupling with the holding area of a lancet as described for example in WO 02/36010 A1. The latter design of a form-fitting coupling between a lancet holder designed as a push rod and a lancet with a holding area has proven to be particularly advantageous when it is intended to use several lancets in the form of a lancet magazine within the scope of the system according to the present disclosure.

An exemplary withdrawal device of the present disclosure may additionally comprises a lancet guide to guide the lancet holder on the predetermined, and optionally straight, puncture path after triggering the lancing movement. The puncturing path optionally runs along a straight line parallel to the main axis (A) of the housing. The lancet guide advantageously enables the lancet holder and thus the lancet held therein or connected thereto to be mechanically coupled to the lancet drive during the entire puncturing process. In this connection, the term "puncturing process" is to be understood within the scope of the present disclosure as the entire movement cycle of the lancet in which the lancet, starting from a resting position located in the housing, is firstly moved in the direction of the exit opening at the proximal end of the housing, emerges there from the housing at least with a part of the lancet tip, reverses the direction of movement at the point of maximum displacement and moves back in the opposite direction until the lancet tip is again located in a position within the housing, optionally until the lancet has again reached its initial resting position. The lancet can in this process be in permanent contact with further guide elements such as for example one or more guide rails. The guide elements or guide rails can for example be mounted on the inner side of the housing of the system according to the present disclosure. Additionally, the guide elements can also be a component of a lancet magazine as described in more detail in the following. For example, the guide elements can be mounted on the inner surface of a magazine housing. Alternatively, the magazine housing itself can also be designed such that it serves as a guide element. Thus, in an exemplary embodiment the individually stored lancets can be stored in individual compartments, such as in individual chambers where the respective chamber walls can serve as guide elements. In this manner it is possible to additionally stabilize the movement of the lancet during the lancing movement and moreover it can enable a permanent contact to be made between the lancet drive and a lancet connected to the lancet holder.

In at least one embodiment of the system according to the present disclosure, the system additionally comprises a lancet drive with an elastic drive element which can be transferred by tensioning from an untensioned into a tensioned state and converted into a puncturing movement by triggering the relaxation movement of the tensioned elastic drive element. During this movement the lancet held by the lancet holder is moved along the predetermined puncture path in the puncturing direction until the lancet tip at least partially emerges from the exit opening and by means of which the lancet holder is in at least one embodiment returned into a position in which the tip of the lancet is located in the housing.

Exemplary elastic drive elements of the present disclosure include springs which can be manufactured from all elastic materials that appear suitable to a person skilled in the art, as well as plastics and metals, such as for example spring steel 1.4310, which can be used in various designs for example as spiral springs or leaf springs. Embodiments of the elastic drive elements can be tensioned in various ways for example by stretching spiral springs along their axes of rotation or optionally by twisting the spiral springs around their axes of rotation. Alternatively, it is also possible to tension leaf springs by deflecting them from their resting position.

Starting with the tensioned state of the elastic drive element that is accomplished in this manner, the relaxing movement of the tensioned elastic drive element is converted into a lancing movement of the lancet holder and thus of the lancet held therein by triggering the drive element. As explained above the lancet held by the lancet holder is moved along the predetermined puncture path in the puncturing direction in the course of this lancing movement, until the lancet tip at least partially emerges from the exit opening and by means of which the lancet holder is returned into a position in which the tip of the lancet is located in the housing, optionally until the lancet holder or the lancet are again in their initial resting position. In at least one exemplary embodiment, the lancet holder and thus also a lancet connected thereto are in a permanent mechanical coupling with the lancet drive. This connection may occur during the entire puncturing and return movement and as a result the lancet drive in at least one embodiment can continuously drive the lancing movement as well as the return movement of the lancet holder or lancet. Such forced-guided drives are known to a person skilled in the art for example in the form of crank gears, lever gears, sliding block guides or cam controls.

At least one embodiment of a drive of the present disclosure includes one that has a transmission by means of which a torque introduced on the input side of the transmission is converted into a longitudinal displacement in the direction of the predetermined puncture path where the longitudinal displacement of the transmission on the output side is transferred onto the lancet holder. Such drives are known for example from EP 0 565 970 A1 as well as EP 1 384 438 A1. The term "transmission" is understood within the scope of the present disclosure in the general sense i.e. as a kinematic device that serves to couple and convert movements. Further, the movement during relaxation of the elastic drive element, optionally by an elastic drive spring, is converted into the movement of the lancet holder or of the lancet held therein in a replaceable manner.

According to at least one embodiment of the system of the present disclosure, the lancet drive has a rotary/sliding transmission with a rotatable drive rotor by means of which a torque introduced on the input side of the rotary/sliding transmission is converted into a longitudinal displacement in the direction of the predetermined puncture path where the drive rotor or the rotary/sliding transmission is coupled to the elastic drive element and the longitudinal displacement of the rotary/sliding transmission on the output side is transferred onto the lancet holder. In this connection, the drive rotor can be rotated about an axis of rotation parallel to the predetermined puncture path as well as about an axis of rotation that is perpendicular to the predetermined puncture path. Within the scope of the present disclosure, the drive rotor may be rotated about an axis of rotation that is parallel to the predetermined puncture path i.e. optionally parallel to the main axis (A) of the housing.

The rotational movement of the drive rotor may be converted into a translational movement parallel to its axis of rotation with the aid of a cam control system, where at least a part of the lancing movement, optionally the return movement, and potentially the entire puncturing and return movement is determined by a relative movement of the guide pin in a recess forming the guide curve, in which the pin travels through the guide curve formed by the recess. In an exemplary embodiment, the rotary/sliding transmission may have a recess that can be rotated with the drive rotor into which a matching guide pin engages, and at least a part of the puncturing and return movement is determined by a relative movement between the guide pin and the recess, in which the guide pin travels through the guide curve formed by the recess. Within the scope of an embodiment of the system according to the present disclosure the recess forming the guide curve that can be rotated together with the drive rotor is designed such that the pin completely or at least partially, travels along this recess when the operating element is actuated in a continuous i.e. uninterrupted movement. In at least one embodiment of the present disclosure, the drive rotor is in the form of a cylindrical sleeve within which is located a piston-shaped part which during the longitudinal displacement in the direction of the puncture path, slides with a cylindrical outer wall within the sleeve.

According to at least one embodiment of the system of the present disclosure, the system has a lancet drive with two rotors where the first is referred to as the tensioning rotor and the second as the drive rotor. These rotors may be linked together by a drive spring as described above and in addition may have the same axis of rotation parallel to the main device axis (A) of the system according to the present disclosure. In this embodiment the tensioning and drive rotor have the same direction of rotation and rotate successively in each case by 360°. For this reason this drive may be referred to as "360° drive". A detailed description of this drive is for example to be found in EP 1 034 740 A1.

The system according to at least one embodiment of the present disclosure additionally comprises a combined tensioning and triggering device with an actuating element that is accessible from the outside of the housing, which has an initial state and an actuated state, wherein the combined tensioning and triggering device has a locking device which is coupled mechanically with the actuating element and lancet drive in such a manner that, when the actuating element is moved along the actuation path, such as towards the proximal end of the system according to the present disclosure, the lancet drive is firstly tensioned and then triggered where the triggering of the lancet drive is enabled when a certain point along the actuation path is reached.

According to at least one embodiment of the present disclosure, the combined tensioning and triggering device serves to tension as well as to trigger the lancet drive described above. It comprises an actuating element which is accessible from the outside of the housing and which can be converted from an initial state into an actuated state by actuation (i.e. displacement). In this connection, the actuating element may be arranged in such a manner that it is at least partially inserted into the housing by the displacement. In an exemplary embodiment, the actuating element is at least partially inserted by the shifting or by the displacement into the end of the housing facing away from the puncture opening also referred to in the following as "distal end" of the housing. In this connection the actuating element is may be arranged such that the displacement occurs along a linear actuation path. This exemplary linear actuation path additionally may run parallel to the puncture movement of the lancet (i.e. parallel to the main axis (A) of the housing). Within the scope of at least one embodiment of the present disclosure, the actuating element represents an operating button projecting from the rear end of the housing facing away from the exit opening for the lancet tip (i.e. the distal end of the housing).

The actuating element which may be referred to as the operating button as described herein has, according to the present disclosure, an initial state and an actuated state and can be converted from the initial state into the actuated state by displacement. In at least one exemplary embodiment, the operating button can be inserted or pressed into the housing in the direction of the proximal end of the housing.

According to the present disclosure, embodiments of the combined tensioning and triggering device may be coupled to a lancet drive in such a manner that the elastic drive element of the lancet drive is converted by a continuous unidirectional displacement of the actuating element, firstly from an untensioned into a tensioned state and is may be subsequently automatically triggered. In this connection the term "continuously" refers within the scope of the present disclosure to a movement that is carried out continuously i.e. without an intermediate standstill of the moved or displaced element where the speed of the movement may vary. The term "unidirectional" is understood within the scope of the present disclosure to mean a movement of the actuating element which is guided along the actuation path without changing the direction of movement where the actuation path may be linear and may run parallel to the puncture direction or to the main axis (A) of the housing.

In at least one embodiment of the present disclosure, the withdrawal device has an operating button which projects from the distal end of the housing and can be wholly or at least partially displaced into the housing by pressing it in towards the proximal end of the housing.

In at least one embodiment of the present disclosure, the actuation of the actuating element may occur by pressing in the operating button at the distal end of the housing towards the proximal end of the housing enables the elastic drive element of the lancet drive to be firstly converted from an untensioned into a tensioned state and subsequently, and directly afterwards in at least one embodiment, to be automatically triggered. The triggering of the puncture operation occurs according to the present disclosure when a predetermined point is reached which the actuating element arrives at during the course of the displacement from the initial state into the actuated state and which may be predetermined by the design of the locking device. This enables the triggering of the puncturing process to occur independently of the force required to tension the spring.

In this connection the term "automatically" is understood to mean that in order to trigger the drive element (i.e. to trigger the lancing movement of the lancet or lancet holder), where no further operations are necessary other than the described continuous unidirectional displacement or pressing in of the actuating element.

Thus, depending on the design of the combined tensioning and triggering device it is possible to freely select which portion of the displacement of the actuating element along the actuation path is firstly utilized to tension the lancet drive or upon reaching which point on the actuation path is the lancet drive triggered. Thus, it is for example conceivable that the actuating element has to be firstly displaced almost over the entire actuation path and the triggering does not occur until the maximum possible displacement has been reached or shortly before. Alternatively it is for example also possible that when half of the maximum actuation path of the operating element is reached, the triggering of the lancet drive already occurs which, however, is associated with a shorter displacement of the actuating element to tension the lancet drive and thus a higher expenditure of force. In this connection it is advantageous that while the operating element is being actuated it is not possible to determine when i.e. at which time during the displacement or pressing in of the actuating element, a triggering of the puncturing process occurs. However, if desired embodiments of the system according to the present disclosure may also comprise suitable means for indicating the imminent triggering of the lancing movement. These suitable means could for example be marks on the housing of the withdrawal system or on the surface of the operating element that are visible or identifiable by touch. The means for indicating the imminent triggering of the lancing movement may be a part of the operating element and may include a mark on the surface of the operating element that is visible or identifiable by touch such as a coloured area or an area that can be distinguished from the remainder of the operating element by its surface finish, such as at the distal end of the actuating element.

According to the present disclosure the combined tensioning and triggering device has a locking device. In principle various technical designs of locking devices provided according to the present disclosure are conceivable in which the mechanical coupling between the actuating element and lancet drive is configured such that, when the actuating element is displaced along the actuation path, the lancet drive is firstly tensioned and then triggered where the triggering of the lancet drive is enabled when a certain point along the actuation path is reached, as described above.

For example, an engagement of a stop element that is permanently connected to the actuating element in the lancet drive can enable it to engage in the drive rotor of the rotary/sliding transmission at least in certain sections when the actuating element is displaced along the actuation path and as a result at least limits and in at least one embodiment prevents its rotatability.

According to at least one embodiment of the system of the present disclosure, the withdrawal device of system comprises a locking device which is designed as a track control and comprises as members a control track part and a control cam where the control cam makes a relative movement with respect to the control track part during at least part of the displacement of the actuating element along the actuation path, in which it at least partially and in some embodiments may completely travel along the control track of the control track part by means of which at least part of the movement of the lancet drive may be is controlled.

Within the scope of at least one embodiment, the control cam is a component of the actuating element or permanently connected to the actuating element. Further, the control track part may be a component of the lancet drive or permanently connected to a component of the lancet drive. Within the scope of at least one embodiment of the present disclosure, the control track part of the track control is completely or at least partially a component of the drive rotor or is mounted on the drive rotor of a lancet drive as described above. In this connection it has proven to be advantageous when the control track is mounted on the outside of the drive rotor but in principle it can be connected to it in other ways for example on the inward facing surface of a drive rotor that may be hollow or have a tubular shape.

An exemplary control cam, according to the present disclosure, may make a relative movement with respect to the control track part during the entire displacement of the actuating element from the initial position into the actuated position. In this process the control cam travels along at least part and optionally the complete control track. In this connection the control track can be designed as a recess in the surface of the respective component of the lancet drive. However, in at least one embodiment the control track is in the form of a rail or also in the form of two rails arranged essentially parallel to one another which projects from the surface of the drive rotor. The control cam can then slide along such a rail or in a track formed by two rails. Further, in at least one embodiment the control track comprises at least one linear section which may run parallel to the axis of rotation of the lancet drive or optionally may run parallel to the axis of rotation of the drive rotor provided it is configured as a component of the drive rotor.

In at least one exemplary embodiment, the control track part comprises a first section and a second section, either or both of which may be linear, where the first section of the control track part runs essentially parallel to the axis of rotation of the rotary/sliding transmission. The terms "essentially parallel" or "essentially perpendicular" as used herein are understood to include within the scope of the entire disclosure slight deviations of up to about 10°, up to about 5°, and up to about 2° (in each case in both directions) from the ideal parallel or perpendicular orientation.

The first section of the control track part may run essentially parallel, and potentially parallel to the axis of rotation of the rotary/sliding transmission or drive rotor provided it is mounted on it (i.e. parallel to the main axis (A) of the housing). The second section of the control track part may run essentially perpendicular, and potentially perpendicular to the axis of rotation of the rotary/sliding transmission or drive rotor provided it is mounted on it. Both sections (i.e. the section which runs essentially parallel to and the section which runs essential perpendicular to the axis of rotation of the rotary/sliding transmission or drive rotor) may be directly linked together such that the control cam can continuously move along them when the actuating element is converted by a continuous unidirectional displacement from an initial state into an actuated state. The control track that is formed has an essentially rectangular course in this design. In at least one embodiment, the control cam firstly runs along the part of the control track part that runs essentially parallel to the device axis and may run parallel to the axis of rotation of the rotary/sliding transmission or the drive rotor. This ensures that the tensioning of the drive element that occurs during the displacement of the actuating element directly changes into a triggering of the lancet drive that is tensioned in this manner and thus the lancing movement of the lancet holder or of the lancet held therein is triggered without further operating steps merely by reaching the end of the first section of the control part running essentially parallel to the axis of rotation of the drive rotor or by reaching the beginning of the second part of the control part oriented essentially perpendicular to the axis of rotation of the drive rotor. In this embodiment, this is ensured by means of the fact that the rotation of the lancet drive and specifically of the drive rotor if the control track is mounted on it, is firstly blocked during the tensioning because the control cam engages in the section of the control track part that runs essentially parallel to the axis of rotation. Then when the end of the section which runs essentially parallel to the axis of rotation is reached or when the second section that runs essentially perpendicular to the axis of rotation is reached, the rotation of the drive rotor is released. The triggering according to the present disclosure of the lancing movement when a predetermined point is reached along the displacement path of the actuating element is determined in this embodiment by the end of the first section of the drive rotor running parallel to the axis of rotation of the drive rotor or by the point at which the first section of the control track merges into the second section of the control track that runs perpendicular to the axis of rotation of the drive rotor. The term running "perpendicular to the axis of rotation" or "perpendicular to the axis of rotation A" in this connection of course also means a section of the control track which runs along a circular track around the lancet drive or a circular section of the control track running along the circumference of the drive rotor.

In at least one embodiment of the control track, the control track may, in addition to the aforementioned first and second sections, also comprise further sections that are not oriented essentially parallel or perpendicular to the axis of rotation of the drive rotor. Thus, for example it may be advantageous to provide sections of the track that are oriented neither parallel nor perpendicular to the axis of rotation of the drive rotor but are at an angle to the axis of up to about 60°, up to about 40°, and up to about 20°. Such sections of control tracks can for example be provided between the aforementioned first and second sections of the control track by means of which the imminent release of the drive rotor (i.e. the imminent puncture can be signalled when the actuating element is operated).

As elucidated above, the actuating element is guided within the scope of at least one embodiment along the actuating path without changing the direction of movement, where the actuating path may be linear, and optionally parallel to the puncturing direction or to the main axis (A) of the housing, and may be guided towards the proximal end of the housing. After the lancing movement of the lancet holder or of the lancet that is firmly connected thereto in a detachable manner, the actuating element may be moved back to its initial position towards the distal end of the withdrawal device, for example by the action of a suitable return spring as is familiar to a person skilled in the art. In this process, the lancet drive or the drive rotor moves back again into its initial position so that the next puncturing operation can be carried out.

According to at least one embodiment of the present disclosure, an exemplary system comprises a lancet drive with a rotary/sliding transmission which has a rotatable transmission member on the input side by means of which a turning moment introduced on the input side of the rotary/sliding transmission is converted into a longitudinal displacement in the direction of a predetermined puncture path. The lancet drive is advantageously mechanically linked to the actuating element such that on the input side of the rotary/sliding transmission the displacement of the actuating element along the actuation path is converted into a rotary movement of the rotatable transmission member in order to tension the rotatable transmission member against the force of the elastic drive element. In this case the axis of rotation of the rotatable transmission member can be oriented perpendicular as well as parallel to the puncture direction or to the main axis (A) of the housing. The axis of rotation of the rotatable transmission member of the rotary/sliding transmission may be oriented parallel to the puncture direction or to the main axis (A) of the housing. This can for example be accomplished in that the input side of the rotary/sliding transmission is formed by a spiral provided on the rotatable transmission member and a tensioning cam connected to the actuating element that can move along the actuation path and slide on a sliding surface of the spiral by means of a contact surface. Such a device is for example known from EP 1 034 740 A1 to which reference is herewith explicitly made. Within the scope of at least one embodiment, the tensioning cam may be permanently connected to the actuating element provided according to the present disclosure.

As already elucidated, at least one embodiment of the system according to the present disclosure comprises a withdrawal device and at least one lancet that is adapted to the withdrawal device. The term "at least one lancet" is understood in this connection to mean that the system comprises either a single lancet or a plurality of lancets. A plurality is understood within the scope of the present disclosure to usually mean a quantity of 2 to about 50, 3 to about 25, 4 to about 10, 5 to 8, 6 or 7, or 6 lancets. The lancets may be held by an embodiment of the lancet holder of the present disclosure such that they can be exchanged so that they can be detached after being used once or if desired several times, from the lancet holder and replaced by another, potentially unused lancet. With regard to improved handling it has proven to be advantageous to provide several lancets in a form stored in a magazine and to provide such a lancet magazine within the scope of the system according to the present disclosure.

In at least one embodiment of the system according to the present disclosure, the exemplary system comprises a magazine containing a plurality of lancets which can be coupled successively to the lancet holder. Such magazines often referred to as "lancing units" are known and are disclosed for example in WO 02/36010 A1. The magazines or lancing units that may be used according to the present disclosure may comprise several lancets which may be each located individually in separated chambers which are surrounded by a magazine housing. The lancets are optionally located within the magazine housing in the resting position (i.e. before the lancing movement and also after the lancing movement). In this manner unintentional injury particularly with an already used lancet can be avoided in at least one embodiment.

Various embodiments of the magazine are designed such that they can be inserted into the housing of the withdrawal device according to the present disclosure. Furthermore, the lancet magazine is designed such that it can be attached to the lancet drive. For this purpose the magazine that can be used according to the present disclosure can for example have the shape of a cap that can be plugged onto the lancet drive. Magazines that can be used according to the present disclosure may have several chambers in each of which one lancet is located which can be successively positioned relative to the lancet drive or to the lancet holder so that the lancet can be coupled to the lancet holder that is designed as a push rod. For this purpose the chambers can be for example be arranged in rows next to one another. However, within the scope of at least one embodiment of the system according to the present disclosure a rotationally symmetric magazine may be used. Such exemplary magazines, also referred to as barrel magazines, have chambers disposed parallel to their axis of rotation and are advantageously inserted into the system according to the present disclosure such that their axis of rotation runs parallel and may run coaxially to the main axis (A) of the system housing. Such an exemplary magazine can be attached automatically to a drive unit or in a manually repeatable manner.

Within the scope of an embodiment of the present disclosure the magazine comprises at least a part of the lancet guide and may comprise the entire lancet guide as disclosed for example in the aforementioned WO 02/36010 A1.

Due to their design the principle of storing lancets in magazines described above often has the consequence that the distance covered by a lancet coupled to the lancet drive during the course of the puncture process is considerably increased in comparison to a lancet that has not been stored in a magazine. This usually also results in larger i.e. more unfavourable dimensions of such withdrawal systems compared to systems without lancets stored in a magazine.

According to at least one embodiment of the lancet according to the present disclosure, the lancets may be furnished with a sterile protection which ensures the sterility of as yet unused lancets and at least of the respective lancet tips until the puncture. Suitable sterile protection bodies are for example those that are removed before using the lancet. Within the scope of the present disclosure, exemplary sterile protection bodies may consist of an elastomeric material this is optionally pierced or stripped off during lancing. In such systems higher drive forces are usually necessary because an additional force input is necessary to strip of or pierce the usually elastic sterile protection.

At last one exemplary system according to the present disclosure allows, optionally due to the locking device provided according to the present disclosure, a considerably more compact design even when using lancets stored in a magazine and in particular lancets that are additionally provided with an individual sterile protection.

Another advantage of various embodiments of the system according to the present disclosure is that the lancet drive or the lancet element is not firstly shifted during use into a tensioned state by tensioning as is the case with comparable devices of the prior art but remains permanently or for a freely determinable time period in this tensioned state until it is triggered in a separate operating step.

A latching or locking of the lancet drive in the tensioned state may also mean that an additional energy input by the user has to be made to reliably latch the locking mechanism or to release the locking mechanism i.e. to trigger the puncture process. In the case of the 360° drive this additional energy input has to be for example generated by an additionally required rotational angle. Thus the coupling of the tensioning and triggering process according to the present disclosure can therefore make it easier to operate because no additional application of force by the user is required. Accordingly, various embodiments of the present disclosure also allow for the use of less powerful drive elements to achieve the same drive forces or speeds. In particular, when spiral springs are used as drive elements, they can then be used with lower force constants. This has considerable advantages with regard to the user having to expend less force, a lower mechanical total load of the system as well as with regard to reduced manufacturing costs.

Furthermore, undesired background noises can be reduced if spiral springs with low force constants are used. Such background noises usually occur when tensioned spiral springs relax and are caused by the coils of the spring striking one another during the relaxation movement especially in the case of spiral springs that are tensioned or released by axial torsion around the longitudinal axis of the spiral spring.

Furthermore, the absence of a further latching of the lancet drive in the tensioned state may result in a considerable and discernible reduction in noise during the operation of the lancet system according to the present disclosure depending on the selected mechanical design. It has turned out that a reduction of operating noises of the lancet system according to the present disclosure as described considerably increases the ease of use especially with regard to a discreet use and thus to a considerably improved acceptance by the user.

Another aspect of the present disclosure concerns a withdrawal device (1) as described above which is suitable for providing the system according to the present disclosure for withdrawing body fluids for diagnostic purposes. Such a withdrawal device may in at least one exemplary embodiment comprise:
  a housing (10) with an exit opening for the lancet tip of
    a lancet adapted to the withdrawal device,
  a lancet holder (20) which can be moved along a predetermined puncture path in the housing (10) to replaceably hold the lancet (91),
  a lancet guide (92) for guiding the lancet holder (20) on
    the predetermined puncture path after triggering the
    lancing movement,
  a lancet drive (30) with an elastic drive element (31)
    which can be converted by tensioning from an untensioned into a tensioned state and by means of which
    after triggering, the relaxing movement of the tensioned elastic drive element (31) is converted into a
    lancing movement in the course of which the lancet
    (91) held by the lancet holder (20) is moved in the
    puncturing direction along the predetermined puncture
    path until the lancet tip emerges at least partially from
    the exit opening and by means of which the lancet
    holder (20) is returned into a position in which the tip
    of the lancet (91) is located in the housing (10), and
  a combined tensioning and triggering device having an
    actuating element (40) that is accessible from the
    outside of the housing (10) which has an initial state
    and an actuated state, where the combined tensioning
    and triggering device has a locking device (70) which
    is mechanically coupled to the actuating element (40)
    and the lancet drive (30) in such a manner that the
    lancet drive (30) is firstly tensioned and then released
    when the actuating element (40) is moved along the
    actuation path where the release of the lancet drive (30)
    is enabled when a certain point along the actuation path
    is reached.

LIST OF REFERENCE NUMERALS 1 withdrawal device
2 proximal end of the withdrawal device
3 distal end of the withdrawal device
10 housing
11 proximal end of the housing
12 distal end of the housing
20 lancet holder/push rod
21 coupling geometry (holding device) of the lancet holder
30 lancet drive
31 elastic drive element
40 actuating element
50 drive rotor
60 cam control
61 lancing curve/lancing profile
62 guide pin
63 driving sleeve
70 locking device
71 control cam
72 first section of the control track part
73 second section of the control track part
80 helical tensioning bolt
81 tensioning cam
82 tensioning sleeve
90 lancet magazine
91 lancet
92 lancet guide
93 holding area of the lancet
94 sterile protection FIGS. 1 and 2 show cross-sections along the main axis of rotation or the main device axis (A) of a system according to the present disclosure which in the form shown comprises a withdrawal device (1) and a lancet magazine (90). FIGS. 3 to 11 show details of the withdrawal device some of which are in a side-view and some in a perspective view. The lancet magazine (90) forms the proximal end (2) of the system and is inserted into the proximal end (11) of the housing (10). The actuating element (40) forms the distal end (3) of the system and projects from the distal end (12) of the housing (10). The system has a lancet drive (30) in the form of a rotary/sliding transmission which is connected via a drive rotor (50) to a tensioning spring in the form of a torsion spring as an elastic drive element (31). The lancet drive is connected on the output side to a lancet holder (20) in the form of a push rod which has a holding device (21) at its proximal end for detachably holding a lancet (91) by form-fitting coupling to its holding area (93) and is connected via a driving sleeve (63, see FIGS. 4 to 10) to a transmission member (50) on the input side. The lancet magazine (90) envisaged in this embodiment comprises a lancet guide (92) which allows the lancet holder and the lancet (91) that is detachably connected thereto to be guided on a predetermined puncture path parallel to the axis of rotation (A) of the system. The lancets stored in the lancet magazine each have a sterile protection (94) which tightly surrounds at least the respective lancet tip. The details are illustrated in the detail enlargement shown in FIG. 1b. In this embodiment the lancet guide (92) is designed as a component of the lancet magazine (90). In cases in which no such lancet magazine is envisaged i.e. in the case of systems according to the present disclosure having individual lancets, the lancet guide can of course also be different such as a component of the housing i.e. attached for example to the inside of the housing.

The drive rotor (50) of the rotary/sliding transmission (output side) is mounted in a fixed axial position relative to the device axis (A) and is linked via the drive spring (31) to an input-side transmission member designed as a spiral-shaped tensioning bolt (80). The tensioning bolt (80) has a helix with a contact surface on which a tensioning cam (81) connected to the actuating element is mounted in a sliding manner. The tensioning cam (81) can also be linked to the actuating element (40) via a tensioning sleeve (82) as shown in FIG. 2.

Before the lancing movement is carried out, one lancet (91) in each case must be coupled to the lancet drive (30). Within the scope of the embodiment shown this occurs by means of a lancet holder (20) designed as a push rod. A thickened holding device (coupling geometry) (21) is provided at the end of the push rod (20) facing the lancet and is inserted into a corresponding holding device in the holding area (93) of the lancet body (91) in order to couple it to a lancet (91). The holding device of the lancet body (91) is designed such that it geometrically couples the holding element (21) of the push rod (20) when the push rod (20) is moved in the puncture direction to such an extent that its front end contacts the lancet body and moves the lancet (91) in the puncture direction. As a result the lancet (91) is coupled in a form-fitting manner to the lancet drive (30). Further details and alternative embodiments of a suitable coupling mechanism are described in the International Patent Application WO 02/36010 A1 the contents of which are made a subject matter of the present application by way of reference.

In the case of the embodiment shown the lancet (91) is "directly guided" i.e. it is located directly in a part of the housing (10) forming the required guide (92) during the lancing movement (in the present case a magazine (90) which contains a plurality of lancets). The embodiment of the lancet drive (30) according to the present disclosure which is elucidated in the following is particularly suitable for such directly guided stored lancets (91). However, it can also be used for the previously very common indirect lancet guides in which the lancet drive is permanently coupled to a lancet holder into which a new lancet is manually inserted for each blood withdrawal. During the puncture process the lancet holder (20) is guided by means of a housing or magazine part (92) serving as a guide and thus indirectly ensures the required guidance of the lancet (91) on its puncture path.

FIG. 3 shows a perspective view of the withdrawal device (1) according to the present disclosure from FIGS. 1 and 2 where the housing (10) and the lancet magazine (90) have been omitted in order to better explain the mode of operation. The withdrawal device (1) that is shown has a locking device (70) that is connected to the actuating element (40) and is designed as a track control (72, 73). The side of the locking device facing the inside of the device (not visible in FIG. 3) has a control cam (71) which is mounted such that it can be moved along a control track (72, 73), where the control track or the control track part (72, 73) is attached to the rotatable drive rotor (50) of the rotary/sliding transmission. As a result the control cam (71) can execute a relative movement in relation to the control track (72, 73) when the actuating element (40) is moved parallel to the main axis of the device (A) during which the said cam slides along the respective section of the control track. The control track of the control track part has two sections (72, 73) within the scope of this embodiment where the first section (72) runs essentially parallel to the main axis of the device (A) i.e. parallel to the axis of rotation of the drive rotor (50) of the rotary/sliding transmission. The first section (72) of the control track crosses immediately over into a second section (73) and this second section (73) is essentially perpendicular to the main axis of the device (A) i.e. perpendicular to the axis of rotation of the drive rotor (50) of the rotary/sliding transmission. The locking device (70) is shown separately again in FIG. 3a. In this case the actuating element (40) is transparent so that the control cam (71) facing the drive rotor (50) is visible.

As shown in particular in FIGS. 4 to 7, the drive rotor (50) that can be rotated about the main device axis (A) is acted upon by the drive element (31) (referred to as drive spring in the following) that is designed as a torsion spring. One end of the drive spring (31) is connected to the drive rotor (50) and the other end is connected to the input-side transmission member which is in the form of a helical tensioning bolt (80). Within the scope of this embodiment the drive spring (31) is tensioned by a rotation of the helical tensioning bolt (80) that acts against its spring force, where the rotation of the helical tensioning bolt (80) is caused by a movement of the actuating element (40) towards the proximal end (2) of the withdrawal system. The axial guided movement, i.e. towards the proximal end of the housing parallel to the main device axis (A), of the tensioning cam that is mounted such that it cannot rotate and is permanently connected to the actuating element (40) said cam being mounted in a sliding manner on the helix of the helical tensioning bolt (80), causes a rotation of the input-side transmission member in the form of a helical tensioning bolt (80) and thus tensions the drive spring (31).

Figure 5:
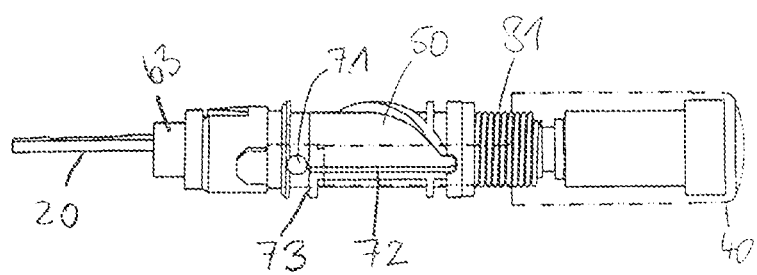
FIG. 5 shows a side-view of the withdrawal device from FIG. 3 where the actuating element is in the actuated state.
Figure 6:
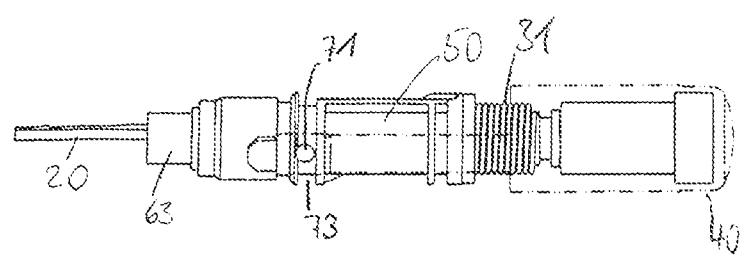
FIG. 6 shows a side-view of the withdrawal device from FIG. 3 with an already rotated drive rotor and a lancet holder shifted in the lancing direction.

FIGS. 4 to 6 illustrate the time course of the mode of operation of the withdrawal device shown in FIGS. 1 to 3. The components shown in relation to each of the previous figures are labelled with the same reference numerals as in the entire present disclosure and are not described again. FIG. 4 shows the withdrawal device according to the present disclosure in the initial state i.e. before moving the actuating element (40). The tensioning cam (not visible) is located within the tensioning sleeve (82). The tensioning cam (71) is at the starting point of the first section (72) of the control track part of the control track running parallel to the axis of rotation of the drive rotor. The actuating element (40) is shown in a transparent manner. The drive rotor (50) of the rotary/sliding transmission as well as the lancet holder (20) are in their initial positions. The actuating element is subsequently converted from the initial state shown in FIG. 4 to the actuated state by movement towards the proximal end (2) of the withdrawal system. In this process the tensioning cam (81) that is located in the tensioning sleeve (82) and is not visible in FIG. 4, slides over the helix of the helical tensioning bolt (80) which rotates the bolt and thus tensions the drive spring (31) against the resting drive rotor (50) that is held by the control cam (71) of the track control. At the same time the control cam (71) that is firmly connected to the actuating element (40) via the locking device (70), moves along the first section (71) of the control track running parallel to the rotational axis of the drive rotor towards the proximal end (2) of the withdrawal system until the control cam (71) reaches the beginning of the second section (73) running perpendicular to the axis of rotation of the rotary/sliding transmission or drive rotor. In this state in which the actuating element (40) is shifted maximally towards the proximal end (2) of the withdrawal device is shown in FIG. 5. In this state the drive rotor (50) begins to rotate about its axis of rotation (A) by the action of the spring force of the tensioned drive spring (31). The propulsion sleeve (63) and the lancet holder (20) which is permanently connected thereto are then still in the initial position at the start of the lancing movement.

FIG. 6 shows a subsequent state of the withdrawal device according to the present disclosure in which the drive rotor (50) has already rotated by about 90° around its axis of rotation and the cam-guided lancet holder (20) is already in a position that is deflected in the puncture direction. FIG. 7 shows the same state of the withdrawal device but viewed from the opposite side. This also shows the output-side of the coupling mechanism designed as a cam control (60).

An output-side coupling mechanism shown in FIGS. 8 to 10 converts the rotary movement of the drive rotor (50) into the puncture movement which is transferred via the lancet holder onto a lancet (91) coupled thereto. The output-side coupling mechanism is formed in the case shown by a cam control (60) having a lancing curve or a lancing profile (61) and a control cam (62) that moves along the lancing curve or the lancing profile (61) during the lancing movement. In the embodiment shown, the guide curve (61) is formed by a circumferential recess running around the circumference of the propulsion sleeve (63). The guide pin (62) is formed on the drive rotor (50) which is enclosed by the part of the propulsion sleeve (63) provided with the lancing curve or the lancing profile (61).

The propulsion sleeve (63) is guided non-rotatably by a longitudinal groove in such a manner that it can only execute a translational movement. The lancet holder (20) is rigidly attached to its front end.

The cam control (60) functions in basically the same manner as the cam controls described in U.S. Pat. No. 5,318,584 and in EP 1 034 740 A1. However, an important difference is that the drive rotor (50) does not have to be turned back during the tensioning of the drive spring (31). As a result it is possible, on the one hand, to select a very simple design of the lancing curve or of the lancing profile (61) and, on the other hand, the entire angle of rotation of 360° can be utilized to convert the rotary movement of the drive rotor (50) into a translational movement of the lancet holder (20) and of a lancet (91) connected thereto.

This can be achieved in that the tensioning device may be constructed according to the present disclosure following the OWADAC principle (one way alternating drive and cocking) as disclosed in EP 1 384 438 A1 to which in this respect reference is herewith made. The end of the drive spring (31) facing away from the drive rotor (50) is supported in this case against an input-side transmission element designed as a helical tensioning bolt (80) which in order to tension the drive spring (31) when the rotation of the drive rotor (50) is blocked can be rotated in the same direction of rotation in which the drive rotor (50) rotates during the puncture movement. During the puncture movement the helical tensioning bolt (80) is locked against backwards rotation so that the drive rotor (50) executes the rotational movement which is converted into the puncture movement of the lancet (91) after the locking device preventing its rotation has been released.

Finally FIG. 11 shows a perspective view of the withdrawal device (1) shown in FIG. 1a with a lancet magazine (90) in place but without the housing (10).

While various embodiments of devices, systems, and methods of withdrawing a body fluid have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A system for withdrawing body fluids, the system comprising:
   a withdrawal device;
   at least one lancet having a lancet body, a lancet tip, and a sterile protection which tightly surrounds at least the lancet tip of the lancet and which ensures the sterility of the unused lancets prior to use in a puncture, the sterile protection comprising an elastomeric material which during the puncture is pierced or stripped off by the lancet tip;
   a housing with an exit opening for the lancet tip, the housing at least partially enclosing the withdrawal device;
   a lancet holder which can be moved in the housing along a predetermined puncture path to replaceably hold the at least one lancet;
   a magazine containing the at least one lancet, wherein the at least one lancet can be successively coupled to the lancet holder;
   a lancet drive with an elastic drive element which can be converted by tensioning from an untensioned state into a tensioned state and by means of which after a triggering, a relaxing movement of the tensioned elastic drive element is converted into a lancing movement in the course of which the lancet held by the lancet holder is moved in a puncturing direction out of the magazine and along the predetermined puncture path until the lancet tip emerges at least partially from the exit opening and by means of which the lancet holder is returned by the lancet drive into a position in which the tip of the lancet is located in the housing;

a lancet guide structured to guide the lancet holder on the predetermined puncture path after the lancing movement is triggered;

a combined tensioning and triggering device having an actuating element and a locking device, the actuating element having an initial state and an actuated state and being accessible from an outside of the housing, the locking device being mechanically coupled to the actuating element and the lancet drive in such a manner that the lancet drive is firstly tensioned during a conversion of the actuating element from the initial state to the actuated state, and then released when the actuating element is converted to the actuated state, wherein the housing at least partially encloses the combined tensioning and triggering device; and an indicating element for indicating an imminent triggering of the puncture movement.

2. The system of claim 1, wherein the locking device is designed as a track control which comprises a control track part and a control cam wherein the control cam makes a relative movement with respect to the control track part during at least a part of the conversion of the actuating element from the initial state to the actuated state, in which it travels along at least part of the control track part of the track control.

3. The system of claim 1, wherein the elastic drive element of the lancet drive is converted by continuous unidirectional displacement of the actuating element firstly from an untensioned state into a tensioned state.

4. The system of claim 1, wherein the actuating element is an operating button protruding out of a rear end of the housing facing away from the exit opening for the lancet tip.

5. The system of claim 1, wherein the magazine comprises at least part of the lancet guide.

6. The system of claim 1, wherein the lancet is mechanically coupled to the lancet drive during the entire puncture process.

7. The system of claim 1, wherein the indicating element for indicating the imminent triggering of the puncture movement is part of the actuating element.

8. The system of claim 1, wherein the magazine is removably coupled to the housing.

9. The system of claim 1, wherein the lancet drive has a rotary/sliding transmission comprising a rotatable drive rotor by means of which a turning moment introduced on an input-side of the rotary/sliding transmission is converted into a longitudinal displacement in the puncturing direction along the predetermined puncture path, wherein the drive rotor is coupled to the elastic drive element and longitudinal displacement of the rotary/sliding transmission on an output side is transferred onto the lancet holder.

10. The system of claim 9, wherein a control track part of a track control is mounted at least partially on the drive rotor.

11. The system of claim 9, wherein a control track part comprises a first and a second section, wherein the first section of the control track part runs essentially parallel to an axis of rotation of the rotary/sliding transmission and wherein the second section of the control track part runs essentially perpendicular to the axis of rotation of the rotary/sliding transmission.

12. The system of claim 9, wherein the rotary/sliding transmission has a cam control comprising a recess forming a guide curve that can be rotated together with the drive rotor into which a matching guide pin engages where at least a part of the puncturing and return movement is determined by a relative movement between the guide pin and the recess which the guide pin makes when it travels through the guide curve formed by the recess.

13. The system of claim 9, wherein the input-side of the rotary/sliding transmission is formed by a helix provided on a rotatable transmission member and by a tensioning cam connected to the actuating element that is configured to slide on a slide surface of the helix during at least part of the conversion of the actuating element from the initial state to the actuated state, by means of a contact surface.

\* \* \* \* \*